(12) United States Patent
Plahey et al.

(10) Patent No.: US 10,806,843 B2
(45) Date of Patent: Oct. 20, 2020

(54) AUTOMATIC DIALYSATE DETECTION IN DIALYSIS MACHINES

(71) Applicant: Fresenius Medical Care Holdings, Inc., Waltham, MA (US)

(72) Inventors: Kulwinder S. Plahey, Martinez, CA (US); John A. Biewer, Waltham, MA (US)

(73) Assignee: Fresenius Medical Care Holding, Inc., Waltham, MA (US)

( * ) Notice: Subject to any disclaimer, the term of this patent is extended or adjusted under 35 U.S.C. 154(b) by 431 days.

(21) Appl. No.: 15/711,111

(22) Filed: Sep. 21, 2017

(65) Prior Publication Data
US 2019/0083692 A1    Mar. 21, 2019

(51) Int. Cl.
*A61M 1/28* (2006.01)
*A61M 1/16* (2006.01)

(52) U.S. Cl.
CPC .......... *A61M 1/284* (2014.02); *A61M 1/1601* (2014.02); *A61M 1/28* (2013.01); *A61M 1/282* (2014.02); *A61M 1/287* (2013.01); *A61M 1/165* (2014.02); *A61M 1/1656* (2013.01); *A61M 1/285* (2013.01); *A61M 1/288* (2014.02); *A61M 2205/12* (2013.01); *A61M 2205/18* (2013.01); *A61M 2205/3331* (2013.01); *A61M 2205/3379* (2013.01); *A61M 2205/3393* (2013.01)

(58) Field of Classification Search
CPC .. A61M 1/1601; A61M 1/165; A61M 1/1656; A61M 1/28; A61M 1/282; A61M 1/284; A61M 1/285; A61M 1/287; A61M 1/288; A61M 2205/12; A61M 2205/18; A61M 2205/3331; A61M 2205/3379; A61M 2205/3393
See application file for complete search history.

(56) References Cited

U.S. PATENT DOCUMENTS

| | | | |
|---|---|---|---|
| 2009/0012457 A1* | 1/2009 | Childers | A61M 1/1605 604/29 |
| 2016/0193400 A1 | 7/2016 | Falkvall et al. | |
| 2017/0128653 A1 | 5/2017 | Yuds et al. | |

OTHER PUBLICATIONS

International Search Report and Written Opinion dated Jan. 1, 2019, in corresponding application PCT/US2018/052034.

\* cited by examiner

*Primary Examiner* — Imani N Hayman

(57) ABSTRACT

A method for operating a dialysis machine to conduct a dialysis treatment on a patient (e.g., a peritoneal dialysis machine) may include transferring dialysate from a first bag, and automatically determining the dialysate from the first bag has completely transferred. After determining the dialysate has completely transferred from the first bag, switching from the first bag to a second bag of dialysate. The method may further include transferring dialysate from the second bag in response to the detection of the completed transfer of the first bag, and automatically determining the dialysate from the second bag has completely transferred. The method may further include determining if the respective first or second bag has completely transferred by comparing a dialysate bag volume transferred to the patient to a detected volume of the respective first or second bag. Systems with dialysis machines for performing such a method are disclosed as well.

28 Claims, 10 Drawing Sheets

AUTOMATIC DIALYSATE DETECTION IN DIALYSIS MACHINES

FIELD OF THE DISCLOSURE

The disclosure generally relates to dialysis machines, and more particularly to an automatic detection method for managing dialysate flow in a dialysis machine.

BACKGROUND OF THE INVENTION

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A dialysis machine, such as a peritoneal dialysis machine, may include one or more bags containing a fluid, e.g., a dialysate for patient infusion. In peritoneal dialysis machines, for example, tubing as one or more fluid lines are inserted into an abdomen of a patient for flowing fresh dialysate and removing used dialysate, waste, and excess fluid. In bags containing fresh dialysate, an amount of air may also be present, for example, due to fill levels and/or osmosis. To reduce or eliminate the potential of delivering air instead of dialysate into the patient's abdomen, the dialysis machine may issue one or more alarms to pause or stop the dialysis treatment. By pausing or stopping the dialysis treatment, the treatment may be prolonged and/or interrupted. As some dialysis treatment occurs overnight, e.g., peritoneal dialysis, the patient may not be aware treatment has stopped, and may not receive the full treatment procedure.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a method for operating a dialysis machine, e.g., a peritoneal dialysis machine, to conduct a dialysis treatment on a patient may include transferring by tubing dialysate from a first bag, and automatically determining the dialysate from the first bag has completely transferred. The method may further include switching from the first bag to a second bag, and then transferring by the tubing dialysate from the second bag in response to the determination of the completed transfer of the first bag. The method may further include automatically determining the dialysate from the second bag has completely transferred.

According to an exemplary embodiment of the present disclosure, a dialysis system for conducting a dialysis treatment on a patient may include a dialysis machine, e.g., a peritoneal dialysis machine, and a first bag or a second bag, or both, connectable to the dialysis machine by a cartridge and tubing. The dialysis machine may be configured to transfer by tubing dialysate from a first bag, and automatically determine the dialysate from the first bag has completely transferred. The dialysis machine may be further configured to switch from the first bag to a second bag, and transfer by the tubing dialysate from the second bag in response to the detection of the completed transfer of dialysate from the first bag, and automatically determine the dialysate from the second bag has completely transferred.

In various of the foregoing and other embodiments of the present disclosure, the dialysate may be transferred directly to the patient via a warmer pouch for in-line heating. According to other embodiments, the dialysate may be transferred to the patient via a heater bag for batch heating. The dialysate may be transferred to the heater bag during a dwell time of the dialysis machine. The dialysate may be transferred to the heater bag to maintain a maximum capacity in the heater bag, thereby minimizing potential alerts or alarms.

In various of the foregoing and other embodiments of the present disclosure, the dialysis machine may automatically determine a volume of the first bag or the second bag, or both, by one or more sensors for detecting a temperature, pressure, air content, flow, or weight, or combinations thereof, of the first bag or the second bag, or both. The one or more sensors of the dialysis machine automatically detect a temperature, a pressure, air content, flow, or weight, or combinations thereof, of the dialysate for determining that transfer of the dialysate is complete.

In various of the foregoing and other embodiments of the present disclosure, the dialysis machine may monitor a total treatment volume of dialysate transferred across all dialysate bags to determine completion of the dialysis treatment. According to embodiments of the present disclosure, the first bag, the second bag, or both, are maintained in a vertical position or an inclined position when connected to the dialysis machine, such that an air content is disposed at a top portion of the first bag, or the second bag, or both.

In various of the foregoing and other embodiments of the present disclosure, the dialysis machine may determine if an air content is detected in the transferred dialysate, such that in response to detecting air content in the transferred dialysate, determining if the dialysate from the respective first or second bag has completely transferred, and in response to detecting no air content in the transferred dialysate, determining if negative pressure is detected in the tubing to the respective first or second bag. When air content is detected in the transferred dialysate, in response to the dialysate completely transferring from the respective first or second bag, additional dialysate bags connected to the dialysis machine for transfer may be determined. In response to the dialysate not completely transferring from the respective first or second bag, an air management check prior to continuing dialysate transfer may be initiated. When no air content is detected in the transferred dialysate, in response to detecting a negative pressure in the tubing to the respective first or second bag, determining if the respective first or second bag passes a line check. In response to not detecting a negative pressure in the tubing to the respective first or second bag, dialysate from the respective first or second bag may continue to transfer. The line check may include flowing a volume of dialysate in reverse back to the respective first or second bag, wherein in response to reaching the respective first bag or second bag, the dialysis machine may determine if the respective first or second bag has completely transferred, and in response to failing to reach the respective first bag or second bag, the dialysis machine may determine the tubing, the first bag, or the second bag, or combinations thereof, is kinked or blocked, or both. The dialysis machine may determine if the respective first or second bag has completely transferred by comparing a dialysate bag volume transferred to a detected volume of the respective first or second bag. When the tubing, the first bag, or the second bag, or combinations thereof is kinked, or blocked, or both, an alarm may be generated.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
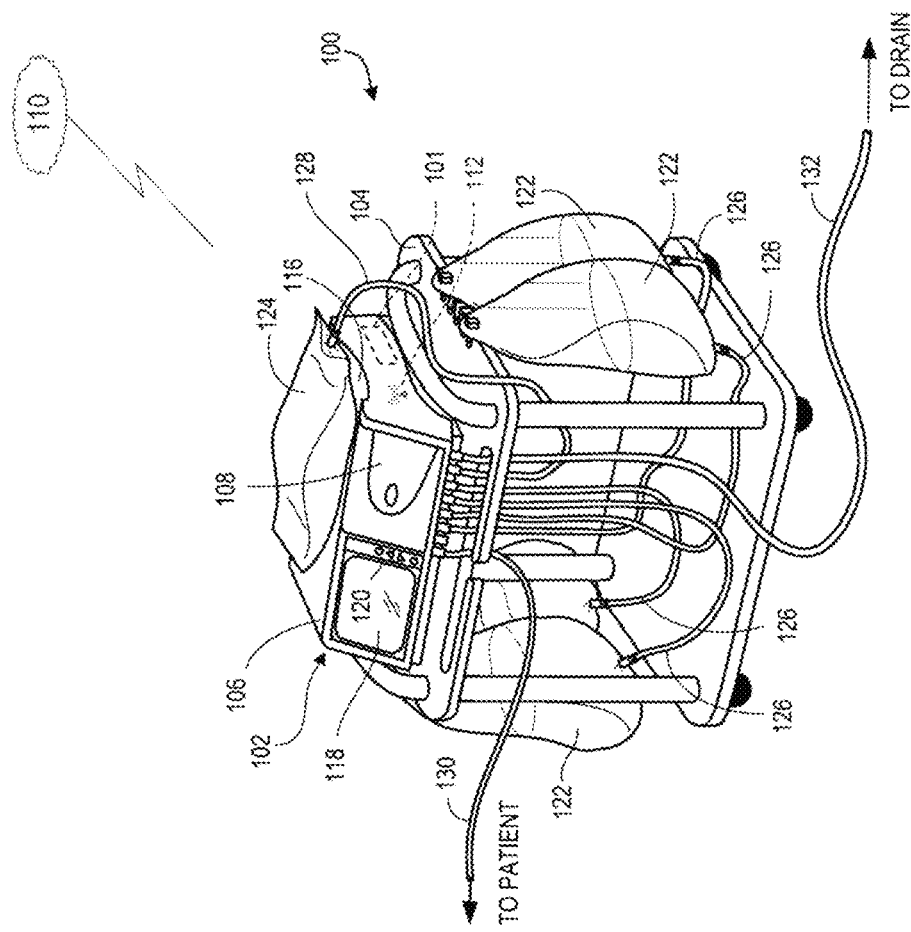
FIG. 1 illustrates an exemplary embodiment of a dialysis system configured in accordance with the present disclosure.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

An exemplary embodiment of a method for operating a dialysis machine may include an automatic detection of dialysate in dialysate bags that are connected to the machine during a dialysis treatment. As described above, each dialysate bag may contain a volume of air (e.g., an air content), which may be present as a result of the bag being not completely filled with dialysate during manufacture. Additionally, dialysate bags may be stored for a period of time prior to sale and/or use by a patient, e.g., 1-2 years or longer. Certain bag materials may be more susceptible to osmosis, for example, a Biofine™ material bag may have a greater volume of air after a period of storage than a bag made of a different material, such as a polyvinyl chloride (PVC) material. However, there are other tradeoffs to one material versus another which are taken into consideration, e.g., the weight that the bag material contributes to the overall weight of the dialysate bag when it is filled. Thus, for example, the ability to manage an air content in a bag, while utilizing a lighter weight material may be advantageous. If the dialysis machine draws a combination of dialysate and an air content (e.g., air bubbles) from one of the bags or elsewhere in the system, the dialysis machine may deliver less than the prescribed volume of dialysate to the patient over the course of the dialysis treatment and/or a potentially painful build-up of excess air in the patient may result. For example, air infused to a patient may result in the patient experiencing shoulder pain as the air moves upward through the body. Although the term "bag" is used throughout, it should be understood that a dialysate bag 122, 124, may be any type of container capable of holding a fluid, e.g., a dialysate. In some embodiments, a fluid container may include a container in which dry concentrates are mixed with water to generate dialysate suitable for a dialysis treatment.

To ensure patients safely receive the proper amount of dialysis treatment, an air content in the dialysis machine may be minimized by sensor detection, alerts, and/or alarms, which may pause or halt the treatment procedure. An alarm may occur in response to detecting an air content, or if a heater bag or a warmer pouch is not detected. An alarm may also be triggered if the dialysis machine does not detect connection with a sufficient number of dialysate bags to complete a treatment. For example, detection of an air content may indicate a dialysate bag is empty, a heater bag is empty, and/or an error in the connection of the tubing, warmer pouch, and/or bags to the dialysis machine. If the patient is awake, pausing or stopping the procedure may allow the patient to check the bags and tubing. However, when patients are sleeping they may be unaware treatment has stopped, and thus may not receive the proper amount of dialysate.

FIG. 1 shows an example of a dialysis system 100 (e.g., a peritoneal dialysis (PD) system) that is configured in accordance with an exemplary embodiment of the system described herein. In some implementations, the dialysis system 100 may be configured for use at a patient's home (e.g., a home PD system). The dialysis system 100 may include a dialysis machine 102 (e.g., a peritoneal dialysis machine 102, also referred to as a PD cycler) and in some embodiments the machine may be seated on a cart 104. The dialysis machine 102 may include a housing 106, a door 108, and a cartridge interface for contacting a disposable cassette, or cartridge, where the cartridge is located within a compartment formed between the cartridge interface and the closed door 108. A heater tray 116 may be positioned on top of the housing 106. The heater tray 116 may be any size and shape to accommodate a bag of dialysate (e.g., a 5 L bag of dialysate) for batch heating. The dialysis machine 102 may also include a user interface such as a touch screen 118 and control panel 120 operable by a user (e.g., a caregiver or a patient) to allow, for example, set up, initiation, and/or termination of a dialysis treatment.

Dialysate bags 122 may be suspended from hooks on the sides of the cart 104, and a heater bag 124 may be positioned in the heater tray 116. Hanging the dialysate bags 122 may improve air management as air content may be disposed by gravity to a top portion of the dialysate bag 122. Although four dialysate bags 122 are illustrated in FIG. 1, any number of dialysate bags may be connectable to the dialysis machine 102, and reference made to first and second bags is not limiting to the total number of bags used in a dialysis system 100. A first dialysate bag 122a and a second dialysate bag 122b used throughout the description herein is only an exemplary embodiment, as the dialysis machine may have additional dialysate bags 122a, . . . 122n. The dialysate bags 122 and the heater bag 124 may be connected to the cartridge via dialysate bag lines or tubing 126 and a heater bag line or tubing 128, respectively. The dialysate bag lines 126 may be used to pass dialysate from dialysate bags 122 to the cartridge during use, and the heater bag line 128 may be used to pass dialysate back and forth between the cartridge and the heater bag 124 during use. In addition, a patient line 130 and a drain line 132 may be connected to the cartridge. The patient line 130 may be connected to a patient's abdomen via a catheter and may be used to pass dialysate back and forth between the cartridge and the patient's peritoneal cavity during use. The drain line 132 may be connected to a drain or drain receptacle and may be used to pass dialysate from the cartridge to the drain or drain receptacle during use.

The touch screen 118 and the control panel 120 may allow an operator to input various treatment parameters to the dialysis machine 102 and to otherwise control the dialysis machine 102. In addition, the touch screen 118 may serve as a display. The touch screen 118 may function to provide information to the patient and the operator of the dialysis system 100. For example, the touch screen 118 may display information related to a dialysis treatment to be applied to the patient, including information related to a prescription.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., weight, air, flos, temperature, and/or pressure sensors, and control the dialysis machine 102 based on the received data. For example, the processing module 101 may adjust the operating parameters of the dialysis machine 102.

The dialysis machine 102 may be configured to connect to a network 110. The connection to network 110 may be via a wired and/or wireless connection. The dialysis machine 102 may include a connection component 112 configured to facilitate the connection to the network 110. The connection component 112 may be a transceiver for wireless connections and/or other signal processor for processing signals transmitted and received over a wired connection. Other medical devices (e.g., other dialysis machines) and components may be configured to connect to the network 110 and communicate with the dialysis machine 102.

Figure 2:
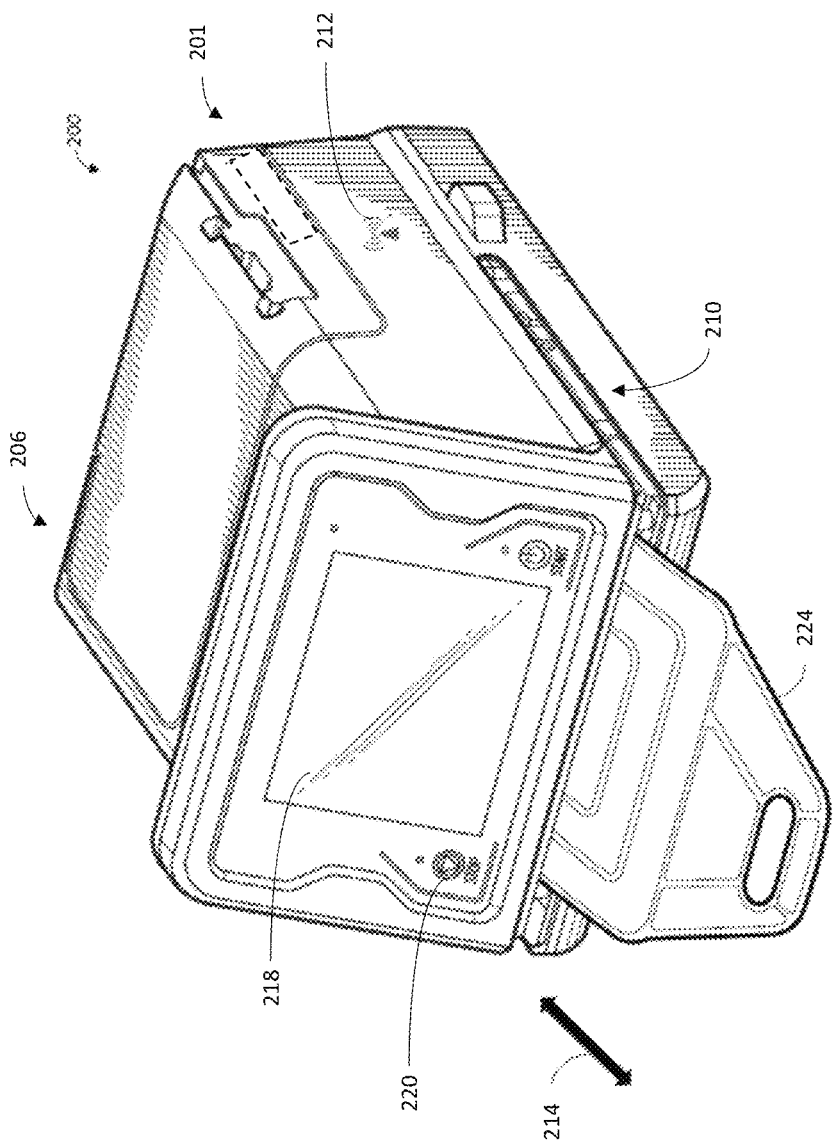
FIG. 2 illustrates another exemplary embodiment of a dialysis machine configured in accordance with the present disclosure.
Figure 2A:
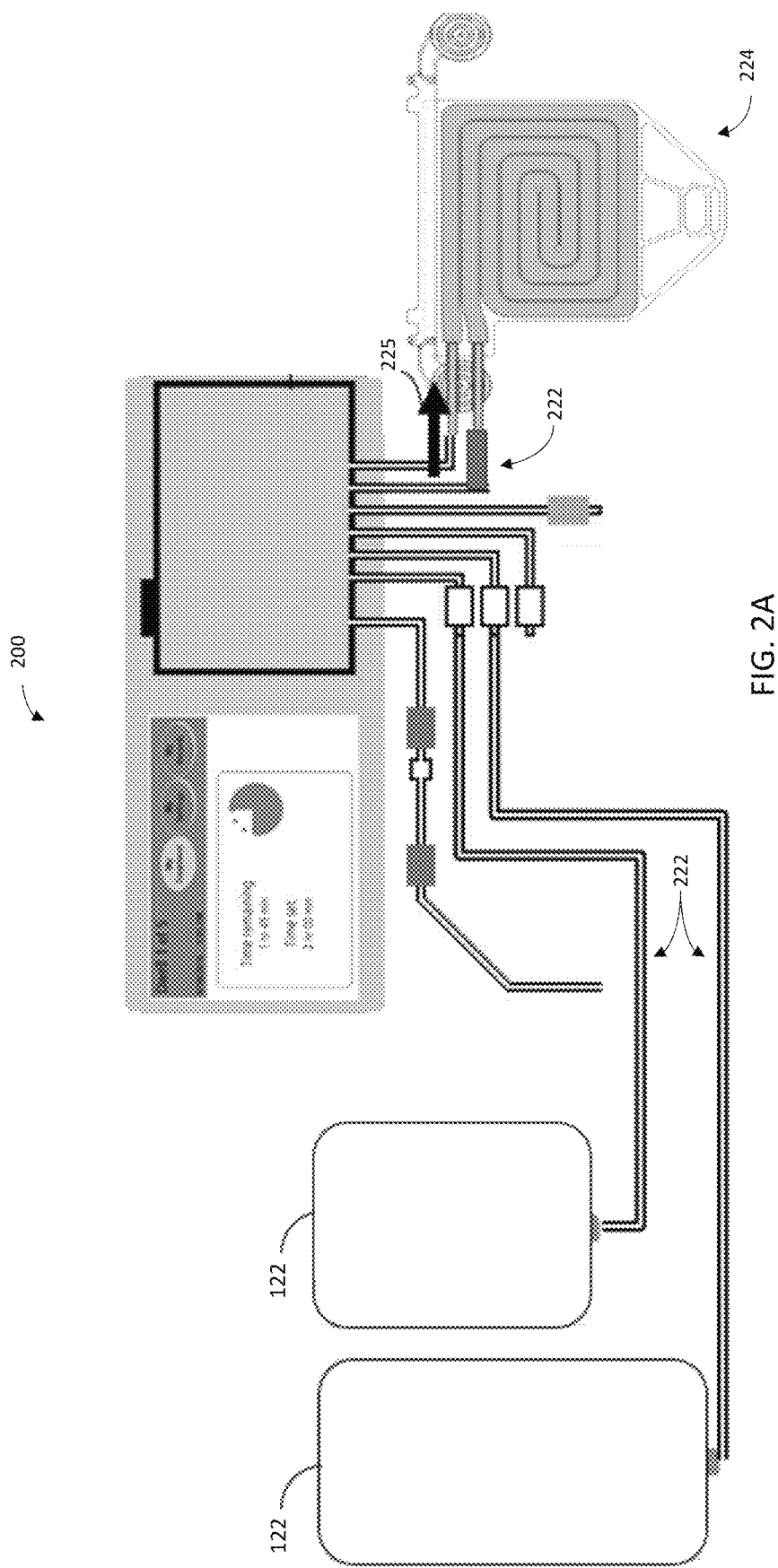
FIG. 2A illustrates an exemplary embodiment of a schematic of a dialysis system for the dialysis machine of FIG. 2 configured in accordance with the present disclosure.

Referring now to FIGS. 2 and 2A, another exemplary embodiment of a dialysis machine 200 in accordance with the present disclosure is shown. The dialysis machine 200 may be implemented in the dialysis system 100 in lieu of the dialysis machine 102, and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment. The processing module 201 and the connection component 212 may be configured similarly to the processing module 101 and connection component 112 described above. However, instead of a heater tray for a heater bag and batch heating being positioned on a top surface 102a of the housing as shown in FIG. 1, one or more heating elements may be disposed internal to the dialysis machine 200. For example, a warmer pouch 224 may be insertable into an opening 210 in a direction indicated at arrow 214. It is also understood that the warmer pouch 224 may be connectable to the dialysis machine 200 via tubing 222, or fluid lines, via a cartridge 215. The tubing 222 may be connectable so that dialysate may flow from the dialysate bags 122, through the warmer pouch 224 for heating, and to the patient.

In such in-line heating embodiments, the warmer pouch 224 may be configured so dialysate may continually flow through the warmer pouch (instead of transferred in batches for batch heating) to achieve a predetermined temperature before flowing into the patient. For example, in some embodiments the dialysate may continually flow through the warmer pouch 224 at a rate between approximately 100-300 mL/min. Internal heating elements (not shown) may be positioned above and/or below the opening 210, so that when the warmer pouch 224 is inserted into the opening 210, the one or more heating elements may affect the temperature of dialysate flowing through the warmer pouch 224. In some embodiments, an internal warmer pouch may instead be a portion of tubing in the system that is passed by, around, or otherwise configured with respect to, a heating element(s). In some embodiments, a dialysis machine 102, 200 may provide an active measurement of the dialysate temperature in dialysate, e.g., in the dialysate bags 122, the heater bag 124, or the warmer pouch 224, or combinations thereof, of FIGS. 1-2A. It is understood that FIG. 1 illustrates that dialysate may be transferable to and stored in the heater bag 124 by "batch" until reaching an acceptable temperature for use, and that FIGS. 2-2A illustrate dialysate continuously flowing through the warmer pouch 224 "in-line" with the dialysis machine 200, reaching an acceptable temperature by the application of internal heating elements.

As described above, embodiments having an in-line warmer pouch 224 may be more susceptible than embodiments utilizing batch heating to temperature variation of the dialysate. For example, if flow rate changes during treatment, such as a kink in the tubing occurring or an obstruction on the inlet, dialysate may dwell in the warmer pouch 224 for a longer time period and reach a higher than intended temperature. If dialysate is higher than approximately 41° C., or 105° F.-106° F., it may not be delivered to the patient to ensure patient safety.

Figure 3:
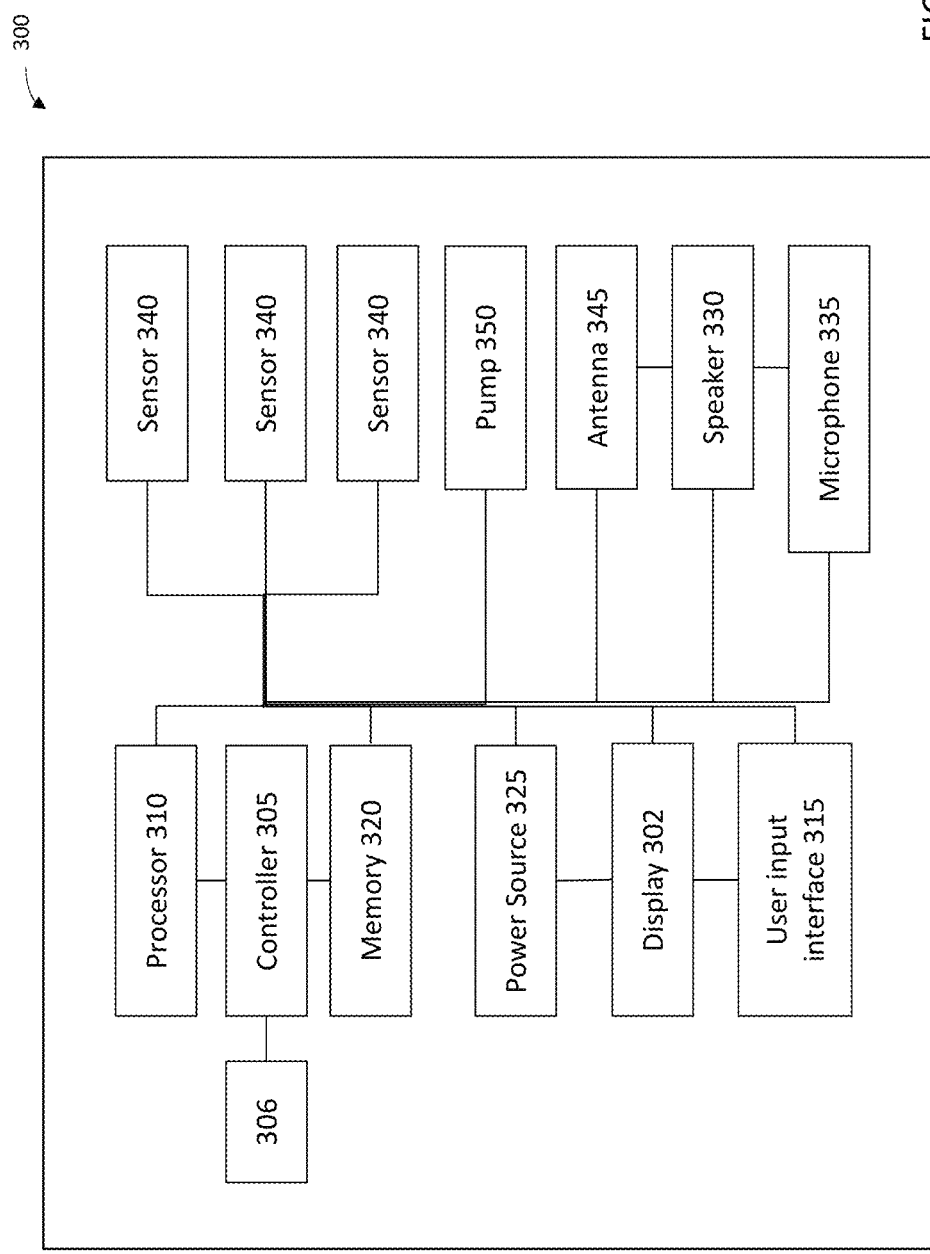
FIG. 3 is a block diagram illustrating an exemplary embodiment of a dialysis machine controller in accordance with the present disclosure.

Referring to FIG. 3, a schematic of an exemplary embodiment of a dialysis machine 300 and a controller 305 in accordance with the present disclosure are shown. The dialysis machine 300 may be a home dialysis machine, e.g., a peritoneal dialysis machine, for performing a dialysis treatment on a patient, and may be included in the system 100 for dialysis machines 102, 200, described above with respect to FIGS. 1 and 2. Additionally, components described with respect to the dialysis machine 300 may also be included in the dialysis machines 102, 200. A power source 325 may provide power and/or a connection to an external power source to the dialysis machine 102, 200, 300, 400.

The controller 305 may automatically control execution of a treatment function during a course of dialysis treatment. For example, the controller 305 in dialysis machine 102, 200, 300, 400 may control the delivery and transfer of dialysate as shown in FIGS. 4A-4E and FIG. 5, and described below. The controller 305 may be operatively connected to sensors 340 and deliver one or more signals to execute one or more treatment functions, or a course of treatment associated with various treatment systems. For example, dialysis treatment may include transferring dialysate from the first bag 122a to the heater bag 124, and then from the heater bag 124 to the patient, and then transferring dialysate from the second bag 122b to the heater bag 124, and then from the heater bag 124 to the patient. In other embodiments, dialysis treatment may include transferring dialysate directly from the first bag 122a to the patient through the warmer pouch 224, and then from the second bag 122b to the patient through the warmer pouch 224, or a course of treatment associated with various treatment systems. In some embodiments, a timer 355 may be included for timing triggering of sensors 340. It is understood that sensors, including but not limited to pressure sensors, weight sensors, flow sensors, air sensors, and temperature sensors, may detect dialysate temperature, fluid volume, air content, fluid flow rate, and fluid flow pressure for the dialysis machine 102, 200, 300, 400 to determine flow delivery to and from the patient. For example, the dialysis machine 102, 200, 300, 400 may include a plurality of sensors for detection and/or measurement of any combination of temperature, pressure, volume, air content, fluid flow. Multiple sensors may also be included to detect and/or measure individually the temperature, pressure, volume, air content, fluid flow.

In some embodiments, the controller 305, processor 310, and/or memory 320 of the dialysis machine 300 may receive sensor 340 signals indicating complete dialysate transfer of the first and/or second bags 122a, 122b, and indicating process parameters, such as temperature, pressure, air content, volume, flow rate, and the like. When an air content is detected, which may be indicative of an empty dialysate bag, the dialysis machine 102, 200, 300 may be configured to close a valve associated with the respective empty dialysate bag 122a, 122b and open a valve associated with a full dialysate bag 122a, 122b. In some embodiments, the memory 320 and the controller 305 may associate dialysate bag sizes with a range of dialysate volume so as to track dialysate transfer for determining when a bag 122 is empty. For example, each bag 122 (e.g., the first bag 122a, the second bag 122b, and the heater bag 124) may contain an approximate amount of dialysate, such that "approximate" may be defined as a 3 L dialysate bag containing 3000 to 3150 mL, a 5 L dialysate bag containing 5000 to 5250 mL, and a 6 L dialysate bag containing 6000 to 6300 mL). Although bag volume is described herein as 3 L, 5 L and 6 L, it is understood that the specified volumes are only exemplary and bag volume may be any volume, and an "approximate" volume may be in a range within 10% of the desired volume.

As described above, the warmer pouch 224 may not retain dialysate for an extended period of time, instead providing a conduit for a constant flow of dialysate through a path for heating the dialysate before flowing into the patient. The controller 305 may also detect connection of the dialysate bags 122, the heater bag 124, and/or the warmer pouch 224. When the controller 305 determines that the dialysate transferred is within the approximate range of volume depending on the bag size, the controller 305 may automatically close the valve of the empty dialysate bag 122 and open the valve of an additional dialysate bag 122.

Sensors 340 may also include weight sensors for weighing any of the first bag 122a, second bag 122b, heater bag 124, or warmer pouch 224, or combinations thereof. As described above, it may be advantageous to maintain the heater bag 124 at a maximum capacity to minimize potential alerts or alarms. In some embodiments, a volume of dialysate larger than the patient fill volume may be transferrable, and may fill during dwell times of the dialysis machine 102, 200, 300 to minimize potential alerts or alarms. A weight sensor may detect the weight of the heater bag 124 so the controller 305, processor 310, and memory 320 may use the weight to determine whether the heater bag 124 is completely filled. In other embodiments, a weight sensor may detect the weight of the warmer pouch 224 so the controller 305, processor 310, and memory 320 may use the weight to determine whether a sufficient constant flow of dialysate is flowing into the patient. In some embodiments, the memory 320 may have stored the weight of bag materials, e.g., Biofine™ and PVC, such that they may be taken into account in the calculations for determining the fluid weight of the heater bag 124 and/or the warmer pouch 224. For example, a Biofine™ material bag may be approximately 50 g, and a PVC bag may be approximately 128 g.

Communication between the controller 305 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In embodiments, the dialysis machine 102, 200, 300 may include at least one pump 350 operatively connected to the controller 305. During a treatment operation, the controller 305 may control the pump 350 for pumping fluid, e.g., fresh and spent dialysate, to and from a patient. The pump 350 may also pump dialysate from the first bag 122a to the heater bag 124, and then from the second bag 122b to the heater bag 124. In embodiments where the warmer pouch 224 is in-line with the dialysis machine 200, the pump 350 may pump the dialysate through the warmer pouch 224 in a direction indicated at arrow 225 directly to the patient (see FIG. 2A). The controller 305 may also be operatively connected to a speaker 330 and a microphone 335 disposed in the dialysis machine 300. A user input interface 315 may include a combination of hardware and software components that allow the controller 305 to communicate with an external entity, such as a patient or other user, and a display 302 may display information to the user or medical professional. These components may be configured to receive information from actions such as physical movement or gestures and verbal intonation. For example, the patient may enter via the user input interface 315 sizes of the dialysate bags 122 for use in treatment. In embodiments, the components of the user input interface 315 may provide information to external entities. Examples of the components that may be employed within the user input interface 315 include keypads, buttons, microphones, touch screens, gesture recognition devices, display screens, and speakers. The dialysis machine 102, 200, 300 may also be wirelessly connectable via the antenna 345 for remote communication.

As shown in FIG. 3, sensors 340 may be included for monitoring one or more parameters and may be operatively connected to at least the controller 305, processor 310, and/or memory 320, or combinations thereof. The processor 310 may be configured to execute an operating system, which may provide platform services to application software, e.g., for operating the dialysis machine 102, 200, 300. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux.

According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, specification of data records for user timing requirements, timing for treatment and/or operations, and historic sensor information. The medium may, for example, be optical disk, magnetic disk or flash memory, among others, and may be permanently affixed to, or removable from, the controller 305.

A pressure sensor may be included for monitoring fluid pressure of the dialysis machine 102, 200, 300, although the sensors 340 may also include any of a heart rate sensor, a respiration sensor, a temperature sensor, a flow sensor, a weight sensor, an air sensor, an air bubble sensor, a video sensor, a thermal imaging sensor, an electroencephalogram sensor, a motion sensor, audio sensor, an accelerometer, or capacitance sensor. In some embodiments, a flow sensor may detect and/or measure a flow of dialysate, e.g., to measure the dialysate transferred from the first and second bags to the patient. In some embodiments, a flow sensor may also detect and/or measure a flow of dialysate through the warmer pouch 224, or to the heater bag 124. It is appreciated that the sensors 340 may include sensors with varying sampling rates, including wireless sensors. Based on data monitored by the sensors 340, patient parameters such as a heart rate and a respiration rate may be determined by the controller 305.

The controller 305 may be disposed in the dialysis machine 102, 200, 300, or may be coupled to the dialysis machine 102, 200, 300, via a communication port or wireless communication links, shown schematically as communication element 306. According to various examples, the communication element 306 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the dialysis machine 300, the controller 305 may be operatively connected to any one or more of the sensors 340, pump 350, or combinations thereof. The controller 305 may communicate control signals or triggering voltages to the components of the dialysis machine 102, 200, 300. As discussed, exemplary embodiments of the controller 305 may include wireless communication interfaces. The controller 305 may detect remote devices to determine if any remote sensors are available to augment any sensor data being used to evaluate the patient.

Figure 4A:
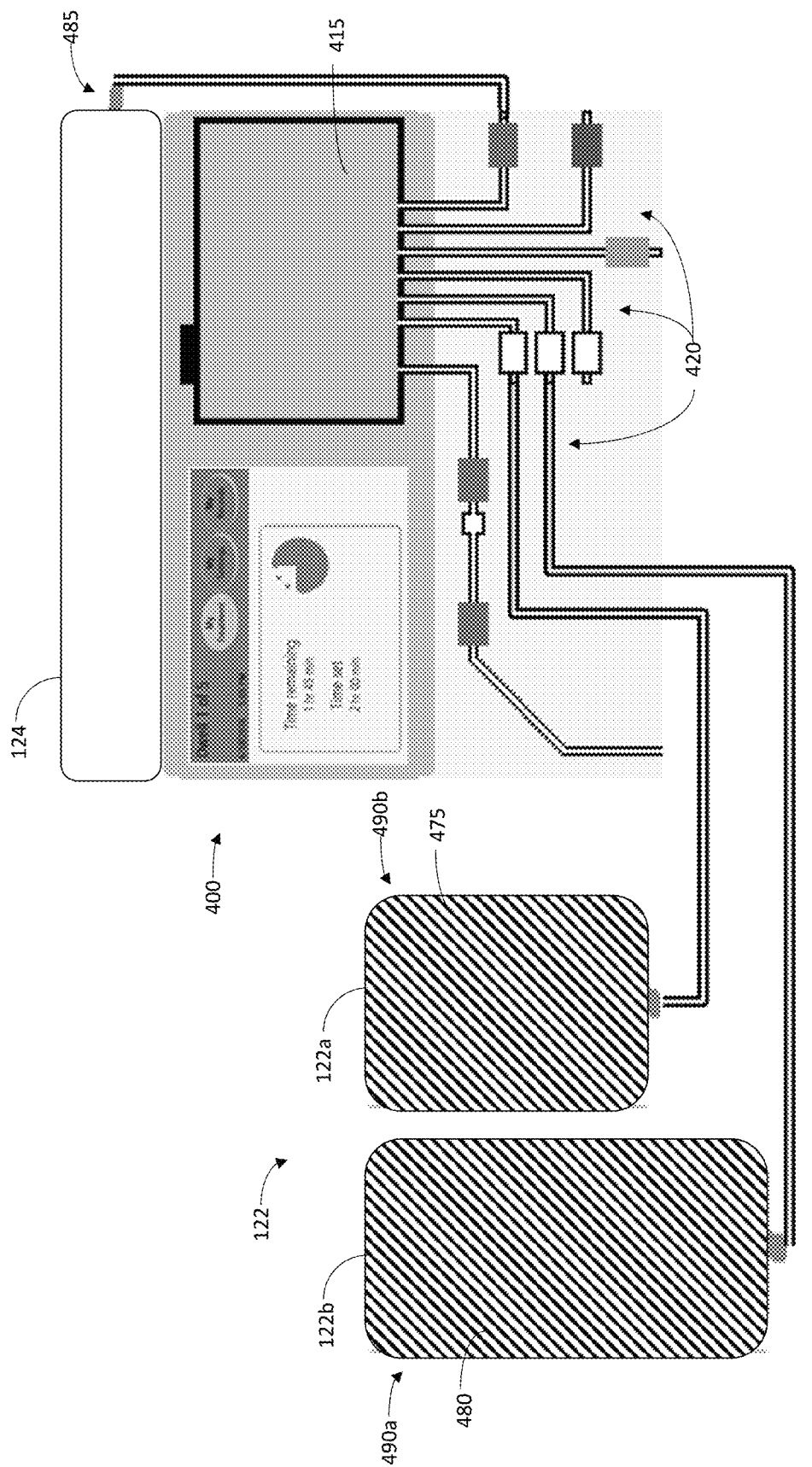
FIGS. 4A-4E illustrates an exemplary embodiment of a dialysis system and a transfer process for a dialysis machine in accordance with the present disclosure.

Referring now to FIGS. 4A-4E, diagrams illustrating an exemplary embodiment of a method for operating a dialysis machine 400 and treating a patient are shown. The dialysis machine 400 may be similar to the dialysis machines 102, 200, 300, and may be incorporated into the dialysis system 100. Although a heater bag 124 is illustrated in FIGS. 4A-4E, for use in a batch heating system similar to the dialysis machine 102, it is understood that the dialysis machine 400 may also instead flow dialysate directly to the patient through in-line heating, such as warmer pouch 224 shown in FIG. 2. FIG. 5 illustrates a flow diagram of an exemplary embodiment of a method for operating a dialysis machine 102, 200, 300, 400 illustrated in FIGS. 4A-4E.

Prior to beginning a dialysis treatment, the dialysis machine 102, 200, 300, 400 may be set up along with other system components. In some embodiments, a cartridge 415 may be insertable or connectible to the dialysis machine 102, 200, 300, 400, with the cartridge 415 including tubing 420. Tubing 420 may be fluid lines described above, e.g., with respect to FIG. 1, including but not limited to dialysate bag lines 126, heater bag line 128, patient line 130, and/or drain line 132. The dialysis machine 102, 200, 300, 400 may include one or more pumps to pump fresh dialysate fluid into a patient via the cartridge 415 and tubing 420, and to remove used dialysate and waste from the patient. The tubing 420 may connect a patient to the dialysis machine 102, 200, 300, 400 and one or more dialysate bags 122, 124 containing fresh dialysate. For example, a first bag 122a, a second bag 122b, a heater bag 124, or a warmer pouch 224, or combinations thereof, may be connectable to the cartridge 415 via tubing 420. As mentioned, additional dialysate bags may also be connected by the tubing 420 to the dialysis machine. In some embodiments, the dialysis machine 102, 200, 300, 400 may connect to the first bag 122a, or the second bag 122b, or both, with the first and second bags 122a, 122b being maintained in a vertical position, e.g., hanging, when connected to the dialysis machine 102, 200, 300, 400 so that an air content present in any of the first bag 122a and/or second bag 122b may be positioned at a top portion 490a, 490b of the first and second bag 122a, 122b, respectively.

It is understood that the individual patient treatment regimen and dialysate bag volume in each bag may dictate how many dialysate bags 122 are connected to the dialysis machine 102, 200, 300, 400. For example, the first bag 122a may contain less dialysate than the second bag 122b, although the first and second bags 122a, 122b may be the same size, or the bag size may be matched approximately to the volume of fluid. A dialysate bag (e.g., the first bag 122a, the second bag 122b, and the heater bag 124) may be sized to contain a range of anywhere from 3 L to 10 L, e.g., approximately 3 L, 5 L, and/or 6 L bags of dialysate. If a patient treatment regimen calls for 9 L total treatment volume of dialysate, a patient may connect a 6 L dialysate bag and a 3 L dialysate bag to the dialysis machine 102, 200, 300, 400 (e.g., each individual dialysate bag may have a bag volume forming a part of the total treatment volume). A dialysis treatment may include approximately 3 L-30 L of dialysate fluid, with dialysis machines connecting a number (e.g., 1 to 5, or more) of dialysate bags having 3 L, 5 L, and/or 6 L, although it is understood that any size dialysate bags may be connected to the dialysis machine.

In embodiments having a heater bag 124 (e.g., see FIG. 1), the heater bag 124 may be placed on a top surface 102a of the dialysis machine 102, 300, 400. The top surface 102a may include a heating element, e.g., a heating tray 116, for heating dialysate in the heater bag 124 before flowing into the patient. In other embodiments, e.g., for in-line heating, the warmer pouch 224 (e.g., see FIG. 2) may be connected in-line to the dialysis machine 200, 300, 400 for dialysate to flow through to heat to a predetermined temperature. For example, the dialysate may be heated up from room temperature in the heater bag 124, or flowing through the warmer pouch 224, to body temperature (approximately 98° F.-100° F., 37° C.).

Once the dialysate bags 122, heater bag 124, warmer pouch 224, cartridge 415, tubing 420, and the like have been set up and connected to the dialysis machine 102, 200, 300, 400, a patient treatment operation may begin. For example, FIG. 4A illustrates an exemplary embodiment of a dialysis machine 400 connected to a disposable set (e.g., dialysate bags 122a, 122b, heater bag 124, and tubing 420) ready for use. As mentioned, instead of the heater bag 124 and top surface 102a, a warmer pouch 224 may be disposable internally to the dialysis machine (see FIG. 2). In dialysis treatment, fluid may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate, ultrafiltrate and/or contaminants/toxins may be flowed out of the patient's abdomen and disposed in a waste container (not shown). This exchange of fresh dialysate and used dialysate after a dwell time may occur for several cycles depending on the patient's treatment regimen. It is understood that sensors, including but not limited to pressure sensors, weight sensors, flow sensors, air sensors, and temperature sensors, may detect dialysate temperature, volume, air content, fluid flow rate, and fluid flow pressure for the dialysis machine 102, 200, 300, 400 to determine flow delivery to and from the patient. For example, the dialysis machine 102, 200, 300, 400 may include a plurality of sensors for detection and/or measurement of any combination of temperature, volume, air content, fluid flow. Multiple sensors may also be included to detect and/or measure individually the temperature, volume, air content, fluid flow. It may be advantageous to track and store the volume of fluid pumped per bag into a memory of the dialysis machine (see FIG. 3) for reference against preset bag volumes for a subsequent comparison verification.

FIG. 5 shows an exemplary embodiment of a flow diagram of a method 500 for operating a dialysis machine, e.g., dialysis machine 102, 200, 300, 400, with the dialysis treatment beginning at step 505, once the dialysate bags 122, heater bag 124, and/or the warmer pouch 224 have been connected to the dialysis machine 102, 200, 300, 400. At step 507, the dialysis machine 102, 200, 300, 400 may determine whether the total treatment volume of dialysate has been delivered to the patient. As described above, the patient may have a total treatment volume of several liters of dialysate across all of the dialysate bags 122, that may be monitored and tracked as dialysate is transferred to the patient in each cycle. Step 507 may be a total treatment volume monitoring, so that the dialysis machine may not deliver more dialysate than the prescribed treatment. If the total treatment volume has been delivered to the patient, the process may end at step 560. In some embodiments, the total treatment volume may account for any dialysate drained due to priming or flushing the machine the before beginning a treatment.

If the total treatment volume has not been delivered to the patient, the process may continue at step 510. At step 510, during the dialysis treatment dialysate may be delivered into a patient from a dialysate bag 122. Dialysate from the first bag 122a and the second bag 122b, and any additional dialysate bags, may be transferrable to the patient via the tubing 420. In some embodiments, dialysate may be transferrable from the first bag 122a, or the second bag 122b, or both (simultaneously or sequentially), to the heater bag 124. For the batch heating using the heater bag 124, at least a portion of dialysate in the heater bag 124 may be used in cycles of dwell time before dialysate from either of the first bag 122a or the second bag 122b is used. In other embodiments, e.g., during in-line heating, the dialysate may flow from the first and/or second bags 122a, 122b directly to the patient via the warmer pouch 224 for heating.

In some embodiments, a dialysis system may be primed, so that at a beginning of a treatment or beginning of delivery from each dialysate bag, prior to delivery of dialysate to a patient, a predetermined amount (e.g., 50 mL to 100 mL) of dialysate may be purged from the system so as to purge any air, for example, air content in the tubing and/or a pump cassette and/or initial air bubbles in dialysate bags/lines. This initial purge, or flush, may also help to remove potential contaminants that may be introduced at connections, e.g., between the bags and the lines, by flowing dialysate in a direction from the dialysate bag to the drain. When the system is primed, the dialysis machine may be configured to purge or drain waste instead of flowing the dialysate into a patient to ensure no contaminants are flowed into the patient.

When dialysate is transferred to the patient, the dialysis machine 102, 200, 300, 400 may draw dialysate from each connected dialysate bag 122 simultaneously. A challenge here is that when the dialysate bags 122 contain differing amounts of fluid, e.g., the first bag 122a may be sized to contain more or less dialysate than the second bag 122b, the dialysis machine 102, 200, 300, 400 may draw air from one of the first bag 122a and dialysate from the other of the second bag 122b. Since some fluid may still be present in a larger bag, e.g., the second bag 122b, the dialysis machine 102, 200, 300, 400 may still draw from each bag, thereby drawing air from the empty bag.

For embodiments having batch heating, a mixture of air and dialysate may be transferred from a bag 122a, 122b, into the heater bag 124, increasing the potential for air content to be delivered to the patient. The dialysis machine 102, 300, 400 may be configured to transfer the dialysate and air content from the bag 122a, 122b only when the heater bag 124 is empty, e.g., all the dialysate in the heater bag 124 may be delivered to the patient before the heater bag 124 is filled again. The dialysis machine 102, 200, 300, 400 may transfer an amount equal to a fill volume (e.g., an amount of dialysate infused into a patient's abdomen) or another predetermined volume of the heater bag 124, plus an additional predetermined amount (e.g., 300 mL) in order to ensure sufficient fluid volume for the next fill. However, air content may still be present in the heater bag 124. For example, the heater bag 124 may lie flat on the top surface 102a of the dialysis machine 102, 300, 400 such that an air content contained in the heater bag 124 may migrate toward a side of the bag, possibly near a connection point 485 of the tubing 420. Some embodiments may account for this by tilting the top surface 102a, so the heater bag 124 is at an incline to have a tubing connector at the lowest side to minimize air content (as air may flow up to an upper portion of the heater bag 124). However, this may not account for user set-up variability, e.g., home use possibly utilizing uneven surfaces. An alert or alarm, or multiple alerts or alarms, may be triggered by a detected air content even though a sufficient amount of dialysate is present.

For embodiments having in-line heating, a mixture of air and dialysate may be flowed through the warmer pouch 224. As an increase in air content flowing through the warmer pouch 224 may result in a decrease in dialysate flowing through the warmer pouch 224, the temperature of the dialysate may be more difficult to control. For example, the heating elements may be driven to heat a larger volume of dialysate than what the system is flowing due to air content, possibly heating a smaller volume of dialysate to a higher than desired temperature. If the temperature of the dialysate exceeds a predetermined temperature limit (e.g., approximately 41° C.), then the dialysate may not be delivered to the patient. This may waste dialysate that could otherwise be delivered to the patient for treatment, reducing the overall volume of dialysate a patient receives during the treatment and thereby potentially reducing overall effectiveness of the treatment.

Even though air content may be detected a sufficient amount of dialysate may still be available for delivery to the patient. It may therefore be advantageous for the dialysis machine to transfer dialysate from a single dialysate bag 122 at a time to reduce the potential of delivering air content to the patient. In some embodiments, the dialysis machine 102, 200, 300, 400 may still be configured to flow dialysate from multiple dialysate bags 122 simultaneously, while monitoring dialysate volume transferred to the patient from each bag. In each scenario, when the volume transferred is within the determined total bag volume of the dialysate bag 122, the dialysis machine 102, 200, 300, 400 may be configured to automatically close a valve of an empty bag, to prevent air content from being delivered to the patient.

Figure 4B:
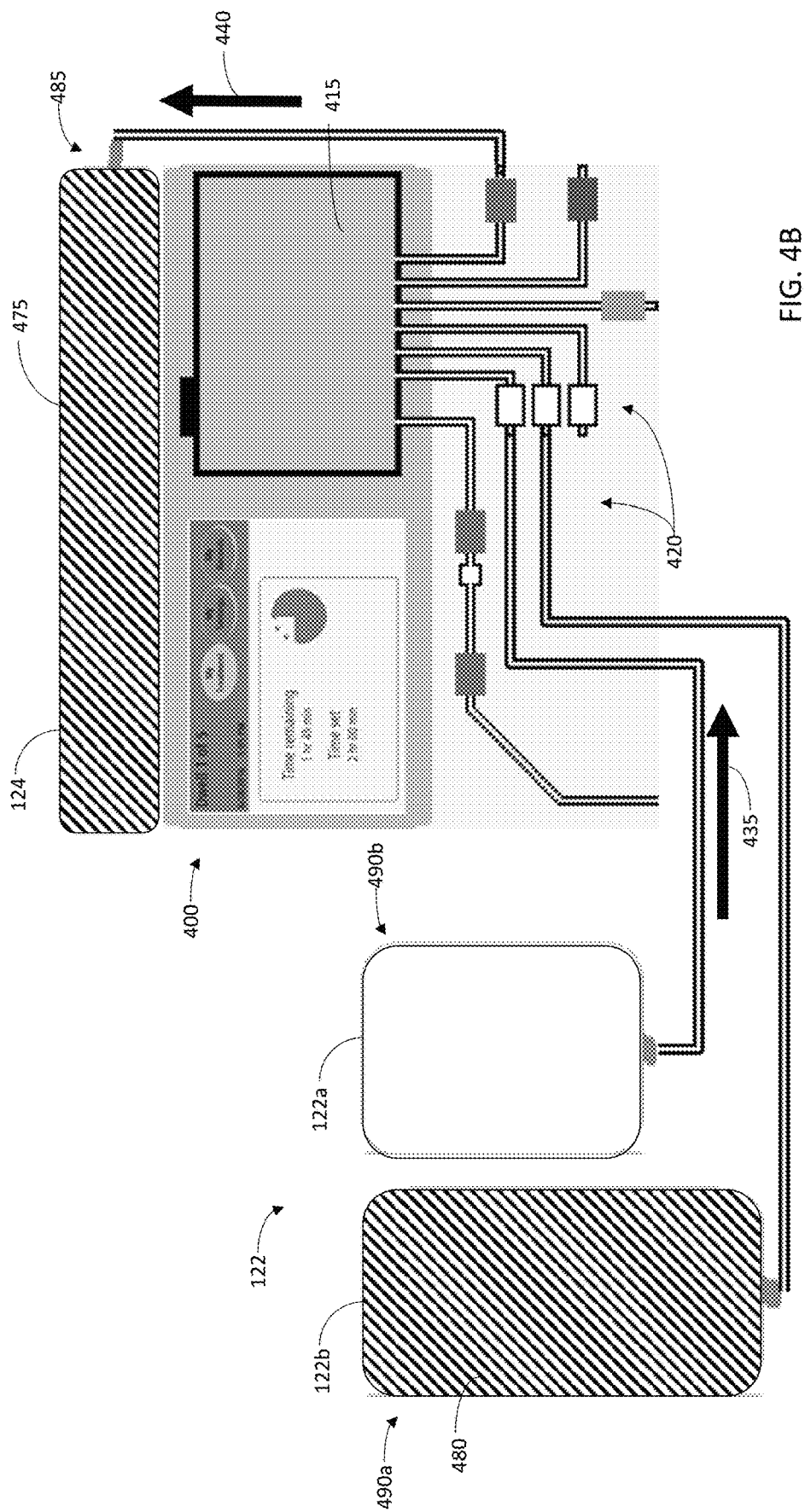
Figure 5:
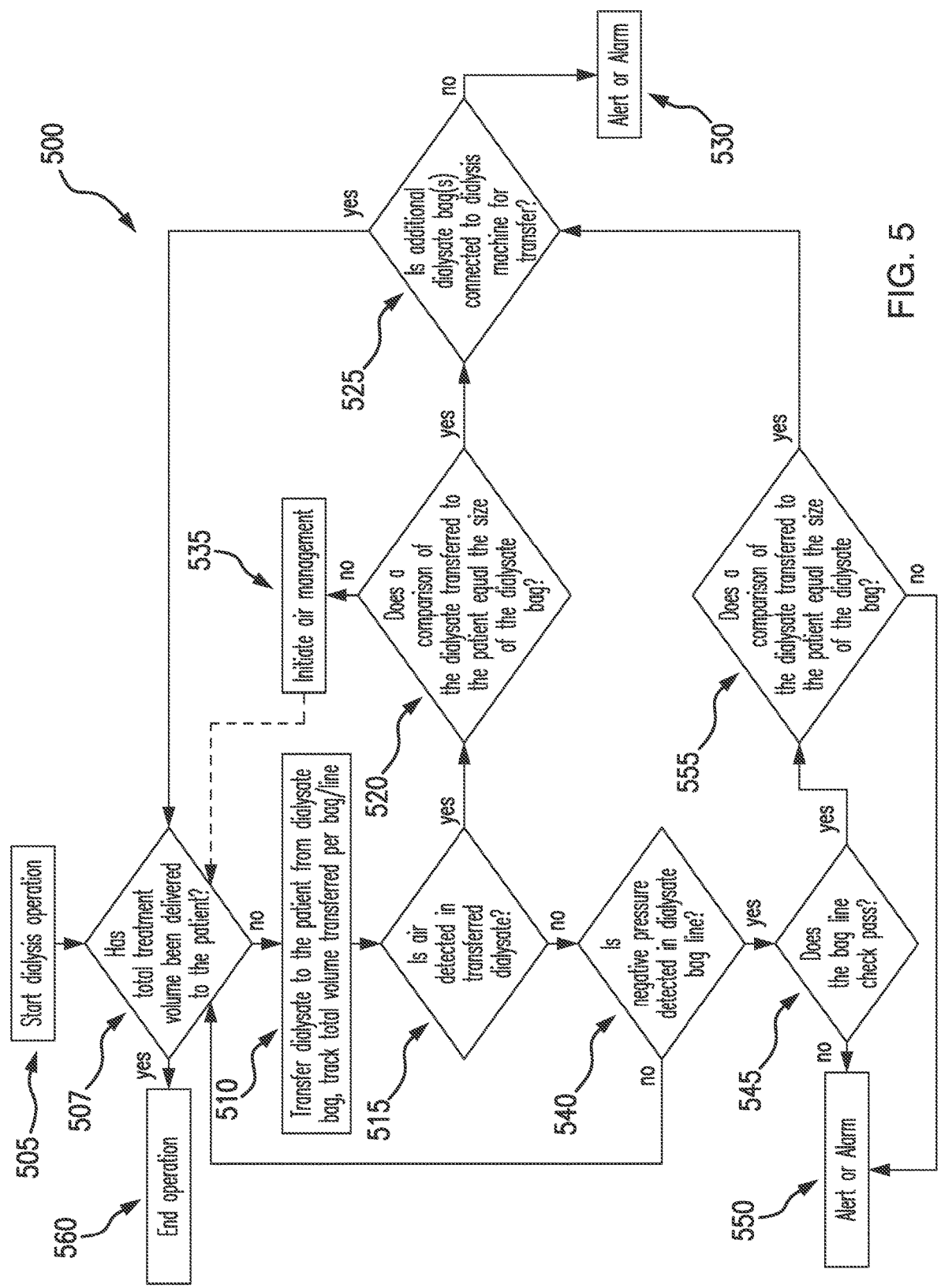
FIG. 5 is a flow diagram illustrating an exemplary embodiment of a dialysis system and a transfer process for a dialysis machine in accordance with the present disclosure.

As shown in FIGS. 4A and 4B, and at step 510 of FIG. 5, a volume of dialysate 475 from the first bag 122a may be transferred to the patient by the tubing 420. For example, in batch heating embodiments, dialysate may flow in a direction indicated by arrow 435 via the cartridge 415 into the heater bag 124 in a direction indicated by arrow 440. The entire content of the bag 122a, e.g., dialysate 475, may be transferred into the heater bag 124 for heating prior to delivery to the patient without transferring any fluid from the second bag 122b, or any additional dialysate bags that may be connected to the dialysis machine 102, 200, 300, 400. The dialysis machine 102, 300, 400 may be configured to maintain a predetermined amount of dialysate 475, e.g., maintaining the heater bag 124 at a maximum capacity to minimize potential alerts or alarms. In some embodiments, a portion of the dialysate 475 larger than the patient fill volume may be transferrable from the first bag 122a after each cycle during dwell time. It may be advantageous to maintain the heater bag 124 at the maximum capacity to shift any air content in the heater bag 124 away from the ports or valves, thereby minimizing potential alerts or alarms.

In embodiments having in-line heating, the dialysate 475 may be transferred directly to the patient after flowing through the warmer pouch 224. For example, the dialysate 475 may flow out of the bag 122a through tubing 420 in a direction indicated by the arrow 435 to flow through warmer pouch 224 for heating, and then delivery to the patient. The warmer pouch 224 may have a pathway for the dialysate to flow through, e.g., a tortuous or circuitous flow path, so that the dialysate may reach the predetermined temperature by the time the dialysate exits the flow path to continue into the patient.

At step 515, the dialysis machine 102, 200, 300, 400 may determine if an air content is detected in the transferred dialysate, e.g., by one or more air sensors and/or pressure sensors 340. Sensors may monitor for air content at periodic intervals during treatment, or may monitor continuously through the treatment. As described above, an air content may be present in the dialysate bags. For example, first and second bags 122 may be connected to the dialysis machine 102, 200, 300, 400 by hanging in a vertical position, thus any air content present in the bags may be positioned at the top portion 490a, 490b of the first and second bags 122a, 122b, respectively. In this configuration, detecting an air content may indicate in some embodiments that all of the dialysate has been transferred out of the dialysate bag 122.

A controller of the dialysis machine 102, 200, 300, 400 may determine if the dialysate has been completely transferred from the first bag 122a. In embodiments, the dialysis machine 102, 200, 300, 400 may transfer at least a portion of the dialysate 475 from the first bag 122a, including for each cycle and dwell time in the case of either batch heating or in-line heating until all of the dialysate 475 has been transferred. When all the dialysate 475, 480 has been transferred out of the first bag 122a, the sensors 340 may detect an air content (e.g., a volume of air). The dialysis machine 102, 200, 300, 400 may be configured to detect an air content, which may signal that the first bag 122a is empty.

In some embodiments, a sensor may monitor a weight of the first and second bags 122a, 122b, heater bag 124, and/or warmer pouch 224 during treatment. For example, the first and second bags 122a, 122b may be weighed by hangers in the system 100 for determining a bag volume of the first and second bags 122a, 122b. The heater bag 124 may be weighed by a weight sensor disposed on the top surface 102a of the dialysis machine 102, 300, 400, and the warmer pouch 224 may be weighed by a weight sensor disposed at the internal heating elements positioned below the opening 210 of dialysis machine 200, 300, 400, to confirm the volume of dialysate passing through the pouch which may be indicative of a flow issue or potential overheating condition. The dialysis machine 102, 200, 300, 400 may correlate a weight of a bag to a volume of dialysate, so that the dialysis machine 102, 200, 300, 400 may automatically update for a treatment based on the individual bag sizes (e.g., bag volume) and the total treatment volume. In some embodiments, a respective bag size may be marked or tagged, e.g., a bar code or other identification, so that the dialysis machine 102, 200, 300, 400 may automatically scan and determine the individual bag sizes and the total treatment volume. It may also be advantageous to sense a weight of the bags for automatically determining a bag size without a user manually entering the information. In this manner, a patient may be able to use different bag sizes without having to remember to update any operating parameters, thereby reducing potential for user error.

If an air content is detected at step 515, the dialysis machine 102, 200, 300, 400 may determine at step 520 if the entire bag volume of dialysate has been delivered. As described above, the dialysis machine 102, 200, 300, 400 may track the volume of dialysate transferred to the patient and/or tracking the weight of the first bag 122a, second bag 122b, heater bag 124, and/or warmer pouch 224. In addition to knowing the approximate bag volume of the dialysate in the respective dialysate bags 122, e.g., 3 L, 5 L, and/or 6 L, the dialysis machine may determine if the detection of air content correlates to the entire contents of the dialysate bag 122 having been transferred from the bag. For example, if the set was primed or flushed prior to the treatment beginning, the bag volume may account for the amount of dialysate that was not transferred to the patient, but diverted and/or drained. Thus, the dialysis machine 102, 200, 300, 400 may compare the total bag volume of dialysate transferred to the known volume of the dialysate bags to determine if all of the dialysate has transferred from the respective first or second bag 122*a*, 122*b*. For example, the volume of dialysate transferred may be the dialysate transferred to the patient, dialysate sent to drain, or otherwise diverted, or combinations thereof.

Figure 4C:
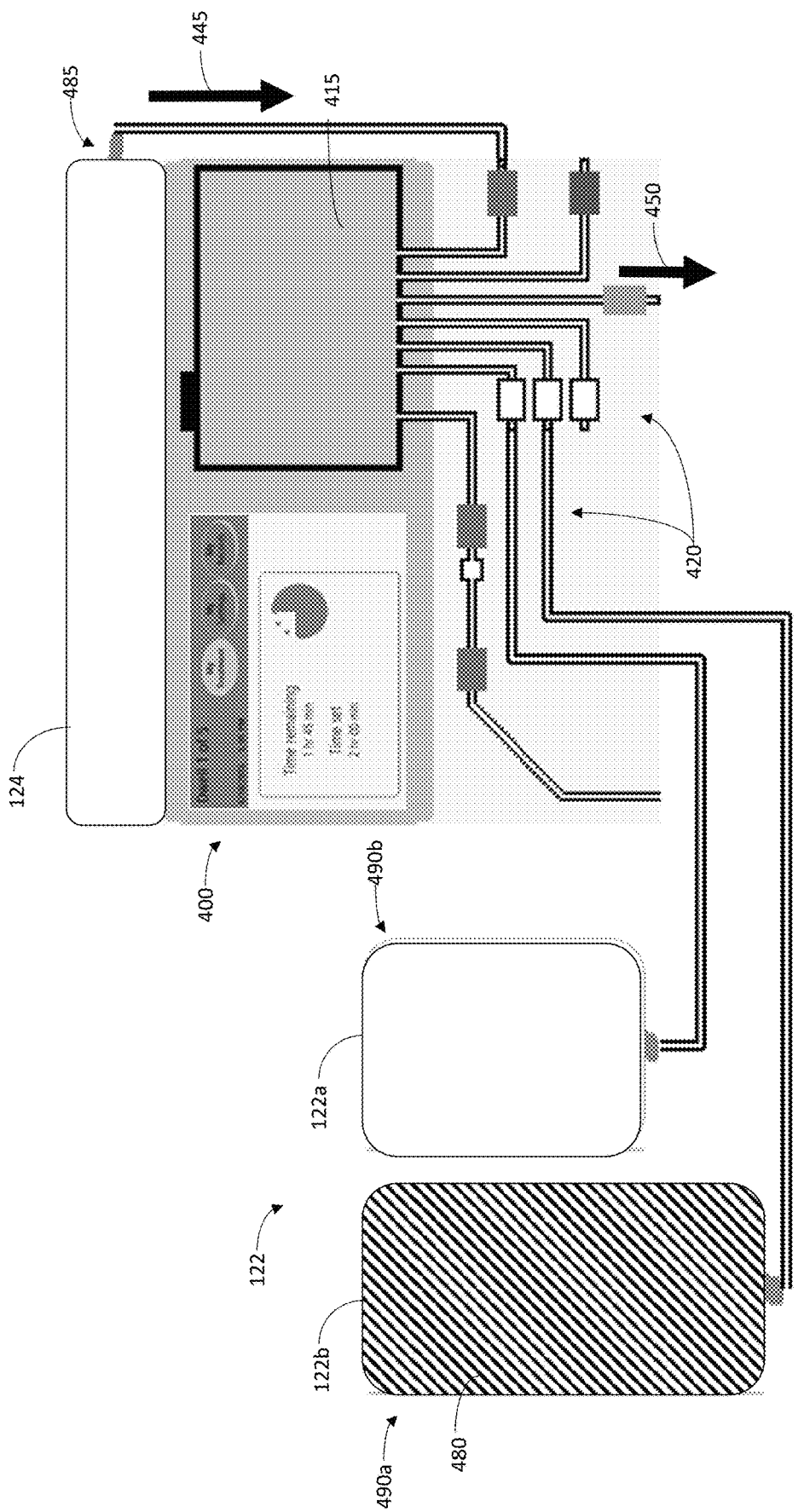
Figure 4D:
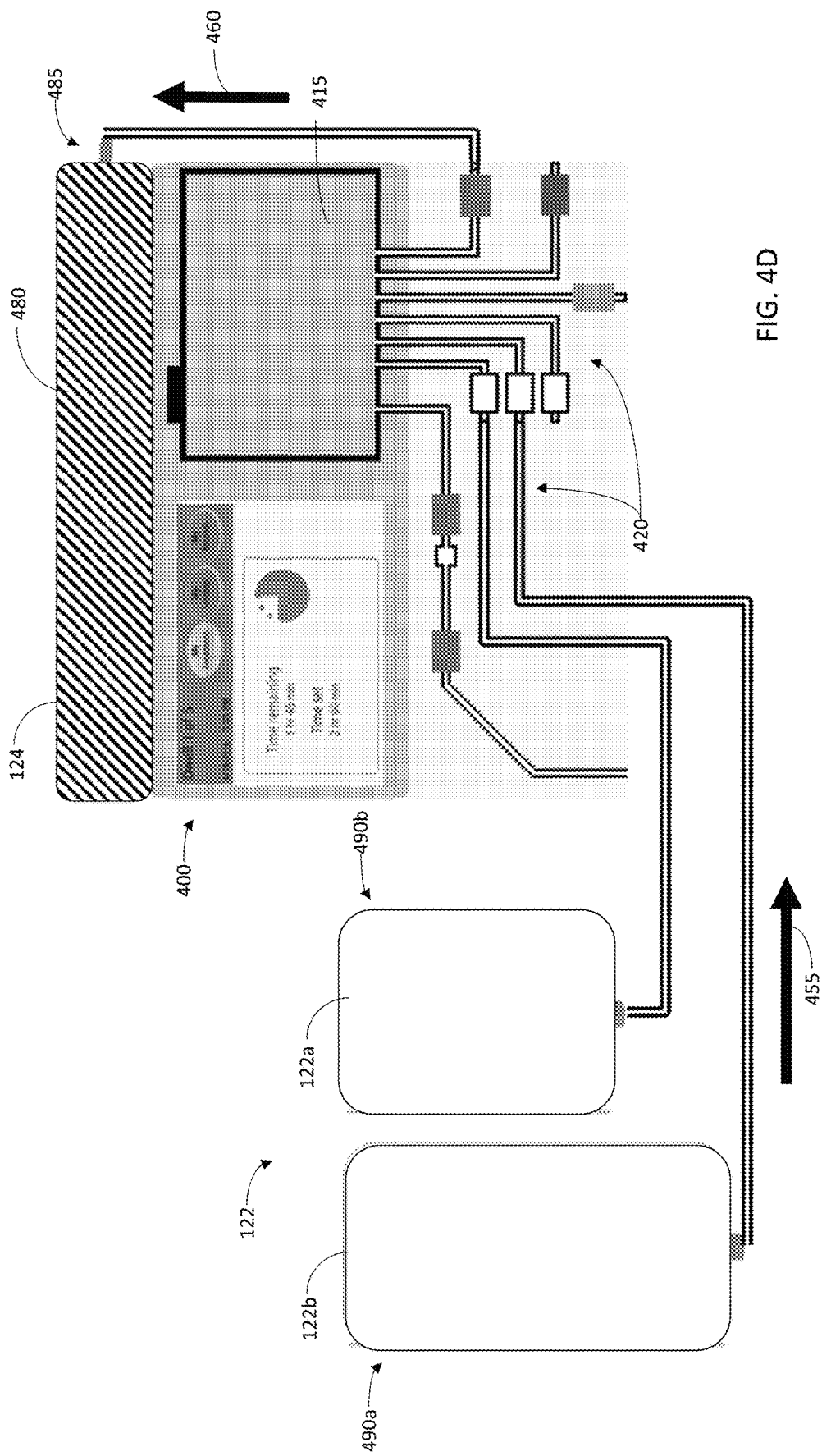

For batch heating, the dialysate 475 may heat up to the predetermined temperature in the heater bag 124, and then flow into the patient by the tubing 420 via the cartridge 415, in a direction indicated by arrows 445 and 450 (see FIG. 4C). The dialysis machine 102, 300, 400 may be configured to maintain a predetermined amount of dialysate 475, e.g., maintaining the heater bag 124 at maximum capacity, by transferring a portion larger than the patient fill volume of the dialysate 475 from the first bag 122*a* after each cycle during dwell time. In embodiments having an in-line warmer pouch 224, the dialysate 475 may flow directly to the patient, heating to a predetermined temperature as it flows through the warmer pouch 224. As described above, for each cycle the dialysis machine 102, 200, 300, 400 may deliver fresh dialysate into the patient's abdomen, hold for a dwell time, and then remove used dialysate, contaminants, and waste out of the abdomen.

If the transfer is complete, the controller of the dialysis machine 102, 200, 300, 400 may automatically switch to the second bag 122*b* for dialysate transfer. When the dialysis machine 102, 200, 300, 400 determines that one of the first bag 122*a* and/or second bag 122*b* may be empty, the dialysis machine 102, 200, 300, 400 may close a valve associated with the respective first or second bag 122*a*, 122*b*, and open a valve associated with the other of the first or second bag 122*a*, 122*b*, for transferring dialysate 475, 480.

If the dialysis machine 102, 200, 300, 400 has delivered the entire contents of the first and/or second bag 122*a* (e.g., FIGS. 4B, 4C), at step 525 the dialysis machine 102, 200, 300, 400 may further determine if additional bags 122 are connected for delivery as part of the patient treatment regimen. As mentioned, a dialysis treatment may include approximately 3 L-30 L of dialysate fluid, which may include connection of a number (e.g., 1 to 5, or more) of dialysate bags 122 to the dialysis machine 102, 200, 300, 400. If the entire dialysate contents have been delivered from all connected dialysate bags 122, or the dialysis machine has otherwise detected that the total treatment volume transferred is within a predetermined percentage of the total treatment volume prescribed for the treatment regimen, the dialysis machine may alert or alarm at step 530. If a treatment volume delivered to the patient is less than a predetermined percentage of the total treatment volume, the dialysis machine 102, 200, 300, 400 may alarm and may shut down without delivering any additional dialysate. For example, if the treatment volume delivered is less than 90% of the total treatment volume, the dialysis machine 102, 200, 300, 400 may alarm or alert a user or medical professional that the treatment may be ineffective. In some embodiments, if a treatment volume delivered to the patient is less than a predetermined percentage of the total treatment volume, but greater than a minimum percentage of the total treatment volume, the dialysis machine may complete treatment but also generate an alarm to notify the user or medical professional of the total treatment. For example, if the treatment volume delivered is greater than 90% of the total treatment volume, but less than 100%, the dialysis machine 102, 200, 300, 400 may complete the treatment but also alarm to notify the user or medical professional. Although the patient may receive an effective level of treatment, the alarm may alert the user to a condition of the dialysis machine 102, 200, 300, 400 to address before beginning another treatment.

If the dialysis machine 102, 200, 300, 400 determines at step 520 that the entire contents of the dialysate bag 122 have not been transferred (e.g., delivered) to the patient, an air management check (e.g., algorithm) may be run at step 535. For example, in order to prevent air content from being delivered to the patient, the dialysate and air content may be sent to the drain for disposal. In some embodiments, the dialysate and air content may be diverted for possible subsequent use later in the treatment, as discussed in co-pending application Ser. No. 15/711,114 filed concurrently, entitled "Dialysis Solution Waste Minimization Systems and Methods" to Biewer et al., which is herein incorporated by reference in its entirety. After the air management check has run, the process may return to step 507 determining if a total treatment volume has been delivered to the patient, and if not, continuing to step 510 for delivering dialysate from the first or second bag 122*a*, 122*b*, with the dialysis machine 102, 200, 300, 400 tracking the volume of dialysate delivered to the patient.

At step 510, if additional dialysate bags are still to be transferred (e.g., 122*b*, . . . 122*n*), then the dialysis machine 102, 200, 300, 400 may continue to deliver dialysate by automatically switching delivery to an additional dialysate bag. When the dialysis machine 102, 200, 300, 400 has transferred the dialysate 475 completely from the first bag 122*a*, dialysate 480 contained in the second bag 122*b* may then be transferred for use in successive cycles. For example, with reference to FIG. 4D, the dialysate 480 may be transferred in the direction of arrow 455 to the heater bag 124, e.g., at step 510 of FIG. 5. In in-line heating embodiments, dialysate 480 may be transferred in a direction of arrow 455 through the warmer pouch 224 via the cartridge for delivery to the patient (see FIG. 2A). Although dialysate 475, 480 may be contained in the first bag 122*a* and the second bag 122*b*, respectively, it is understood that the dialysate 475, 480 may be of the same concentration.

Figure 4E:
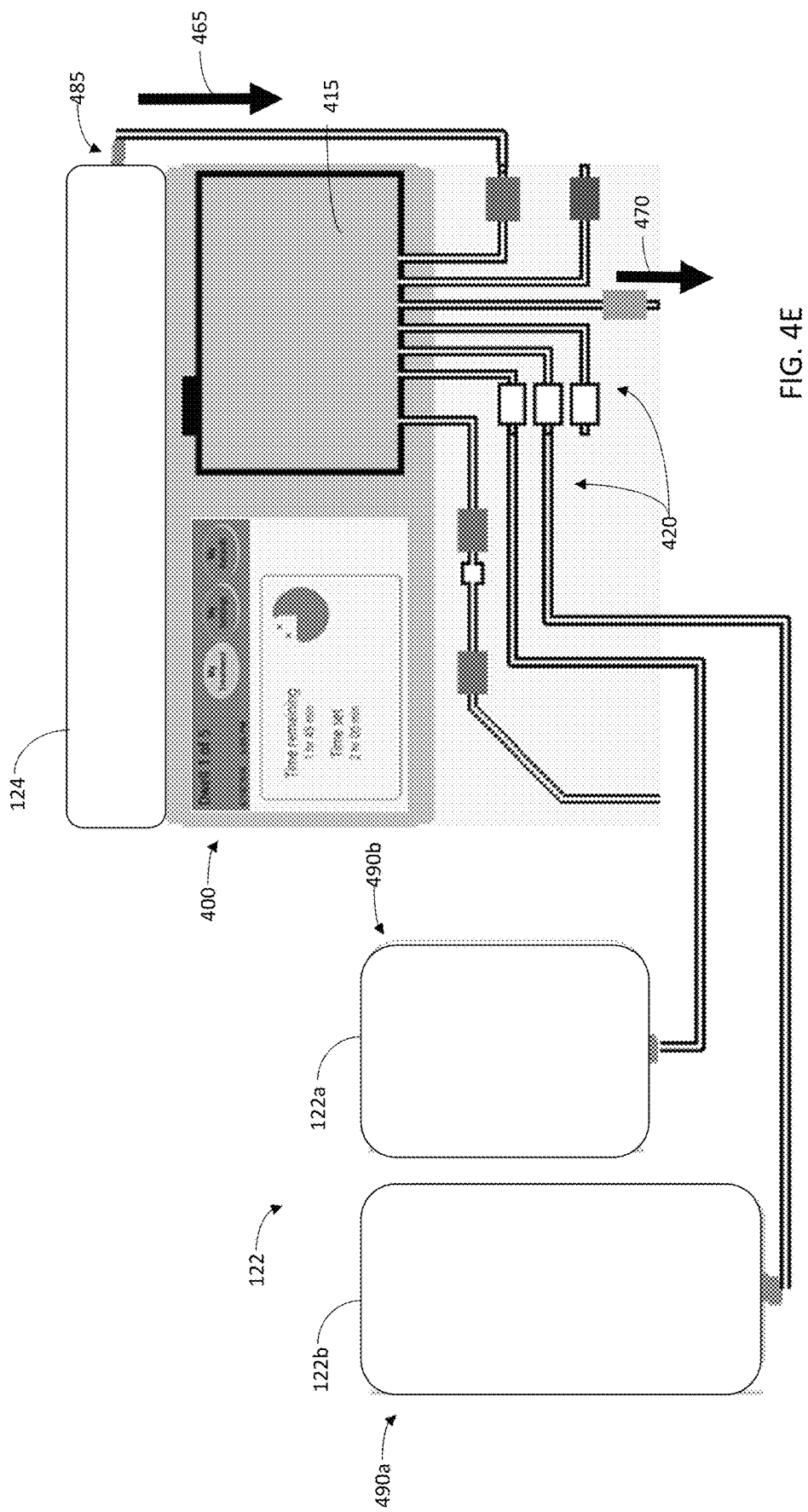

After the dialysate 475 has been transferred, dialysate 480 may then be transferred to the patient. FIG. 4E shows that the dialysate 480 may heat up to the predetermined temperature in the heater bag 124, and then flow into the patient by the tubing 420 via the cartridge 415, in a direction indicated by arrows 465 and 470. As described above, for each cycle the dialysis machine 102, 200, 300, 400 may flow fresh dialysate into the patient's abdomen, hold for a dwell time, and then flow used dialysate, contaminants, and waste out of the abdomen. A patient may undergo a plurality of cycles through the course of an overnight treatment, using the dialysate 475 from the first bag 122*a* before the dialysate 480 from the second bag 122*b*, and any subsequent fluid bags 122 that may be connected to the dialysis machine 102, 200, 300, 400.

In some embodiments, the entire contents of the bag 122*b*, e.g., dialysate 480, may be transferred without transferring any fluid from any other dialysate bag 122 that may be connected to the dialysis machine 102, 200, 300, 400. For batch heating embodiments, dialysate 480 may flow into the heater bag 124 by the tubing 420 via the cartridge 415 in a direction indicated by arrows 455, 460, and from the heater bag to patient in a direction indicated by arrows 465, 470. In embodiments having an in-line warmer pouch 224 (e.g., dialysis machine 200), the dialysate 480 from bag 122b may flow directly to the patient via the warmer pouch 224. The dialysate 480 may flow from the second bag 122b by the tubing 420 via the cartridge 415 in a direction indicated by arrows 455, 470 (see FIGS. 4D, 4E).

Although in some embodiments the entire contents of the first bag 122a may be transferred before the entire contents of the second bag 122b, the order of the dialysate transfer from each dialysate bag 122 is not critical, and in some dialysis systems, dialysate may be infused from different dialysate bags in different orders. Additionally, as described above, in some embodiments, the dialysis machine 102, 200, 300, 400 may transfer dialysate from a plurality of dialysate bags simultaneously while individually tracking dialysate volume drawn from each dialysate bag. In batch heating embodiments, the dialysis machine 102, 300, 400 may transfer at least a portion of the dialysate 480 from the second bag 122b to the heater bag 124 for each cycle and dwell time until all of the dialysate 480 has been transferred. For example, the dialysis machine 102, 300, 400 may be configured to maintain a predetermined amount of dialysate 480, e.g., maintaining the heater bag 124 at maximum capacity. In some embodiments, a portion larger than the patient fill volume of the dialysate 480 may be transferrable from the second bag 122b after each cycle.

For batch heating embodiments, the dialysate 480 may heat up to the predetermined temperature in the heater bag 124, and then flow into the patient by the tubing 420 via the cartridge 415, in a direction indicated by arrows 455, 460, 465, and 470. For in-line heating embodiments, the dialysate 480 may heat up to the predetermined temperature while flowing through the warmer pouch 224 and flowing directly into the patient indicated by arrows 455 and 470. As described above, for each cycle the dialysis machine 102, 200, 300, 400 may flow fresh dialysate into the patient's abdomen, hold for a dwell time, and then flow used dialysate, contaminants, and waste out of the abdomen. A patient may undergo a plurality of cycles through the course of an overnight treatment, using the dialysate 475 from the first bag 122a before the dialysate 480 from the second bag 122b, and any subsequent dialysate bags 122 that may be connected to the dialysis machine 102, 200, 300, 400.

The dialysis machine 102, 200, 300, 400 may continue to draw dialysate from any additional dialysate bags 122 in the same manner described above with respect to the first and second bags 122a, 122b to complete dialysis treatment, looping from step 525 to 507 until the dialysis machine 102, 200, 300, 400 detects that the total treatment volume has been attained, upon which the operation may end at step 560.

If at step 515 an air content is not detected in the delivered dialysate, the dialysis machine 102, 200, 300, 400 may then determine whether negative pressure is detected in the respective bag 122a, 122b, . . . 122n and respective tubing 420 at step 540. Sensors may detect the negative pressure at step 540 at periodic intervals during treatment, or may be continuously monitored during treatment. If negative pressure is detected at step 540, at step 545 the dialysis machine 102, 200, 300, 400 may run a line check to verify dialysate transfer from the first and/or second bag 122a, 122b to the patient. A line check may be performed by the controller 305 to check if the first and second bags 122a, 122b are empty, if the tubing 420 has become kinked (e.g., the patient shifted positions during an overnight treatment, blocking fluid flow) or otherwise blocked, and/or if the first bag 122a and/or the second bag 122b has become kinked or blocked, e.g., formed a condition similar to a duckbill valve, where a portion of a flexible container of the bag 122 may prevent dialysate from flowing to the patient. It is understood that the tubing 420 and the first and/or second bags 122a, 122b may individually become kinked or blocked, or all components may become kinked or blocked during a treatment, e.g., if a patient shifts during treatment, or other condition occurs.

The dialysis machine 102, 200, 300, 400 may perform a line check by temporarily reversing fluid flow, so that a volume of dialysate may be flowed in reverse via the tubing 420 (e.g., tubing 420, including but not limited to dialysate bag lines 126, heater bag line 128, patient line 130, and/or drain line 132) back into the respective first and second bags 122a, 122b.

If fluid flow back into the respective first bag 122a and/or second bag 122b is unsuccessful, e.g., pressure in the tubing 420 may increase without flowing fluid all the way back to the respective first and second bag 122a, 122b, then the dialysis machine 102, 200, 300 may determine that the tubing 420, the first and/or second bag 122a, 122b, or combinations thereof, has become kinked and/or blocked. This may indicate that the respective first or second bag 122a, 122b may not have completed dialysate transfer to the patient. In this instance the dialysis machine 102, 200, 300 may alert the patient by alarm or other notification to check the tubing 420. An alert or alarm at step 550 may alert a patient to the status to check the tubing 420, first and second bags 122a, 122b, connections, and the like. In some embodiments, the alarm may also pause and/or stop the treatment until the condition is removed. For example, a treatment may be delivered to a patient while the patient is sleeping. The patient may turn over on the tubing 420, thereby causing the kink or blocking delivery. The dialysis machine 102, 200, 300, 400 may need to pause until the patient has awoken to readjust the tubing 420. When the tubing 420, first and/or bag 122a, 122b, or combinations thereof, is no longer kinked or otherwise blocked, the dialysis machine 102, 200, 300 may continue the treatment to draw fluid from the respective first and second bag 122a, 122b.

If negative pressure is not detected at step 540, e.g., fluid successively flows back into the respective first and/or second bag 122a, 122b, then the dialysis machine 102, 200, 300, 400 may determine that the tubing 420, the first and/or second bag 122a, 122b, or combinations thereof, has not become kinked or otherwise blocked. This may be indicative that not all the dialysate has transferred from the dialysate bag. In some instances, a larger dialysate bag (e.g., a 5 L, 6 L bag) may be inadvertently connected to the dialysis machine 102, 200, 300, 400 when the dialysis machine 102, 200, 300, 400 understands a smaller dialysate bag is connected. For example, the dialysis machine 102, 200, 300, 400 may incorrectly detect the bag and/or a user may enter in incorrect information. The dialysis machine 102, 200, 300, 400 may continue to deliver dialysate from the larger bag until entirely transferred, and may continue as described, until a full treatment has been attained, by monitoring the total treatment volume provided to the patient, and automatically ending the treatment when the prescribed amount has been attained, regardless of how much dialysate may be left in a dialysate bag. In this manner, the dialysis machine 102, 200, 300, 400 may override the treatment process to only provide the prescribed treatment amount.

When the dialysis machine 102, 200, 300, 400 detects a negative pressure but passes a line check, the entire contents of the dialysate may have been transferred, which is determined at step 555. At step 555 the dialysis machine 102, 200, 300, 400 may determine if the entire content of the dialysate bag has been transferred, e.g., by comparing the volume of dialysate transferred of the dialysate bag 122 to the patient to the bag volume of the dialysate bag. Similar to step 520, the dialysis machine may automatically track the total bag volume of dialysate transferred to the patient, and may therefore be able to calculate if the delivered dialysate bag volume is approximately equal to the total bag volume in the first and/or second bag 122a, 122b. In some embodiments, the bag volume may account for dialysate used to prime or flush the set prior to beginning treatment that is sent to drain. For example, as described below, each bag containing 3 L, 5 L, and/or 6 L may include an additional amount of dialysate to compensate for osmosis during storage. In some embodiments, the dialysis machine 102, 200, 300, 400 may monitor the weight of the dialysate bags, for a comparison of the weight of the bag to indicate when a bag may be empty, e.g., when all of the dialysate has been transferred to the patient.

If the comparison of the dialysate transfer substantially equals the bag volume of the dialysate bag (e.g., the volume transferred is within an approximate range, a 3 L dialysate bag containing 3000 to 3150 mL, a 5 L dialysate bag containing 5000 to 5450 mL, and a 6 L dialysate bag containing 6000 to 6300 mL), the process may return to step 525 to determine if additional dialysate bags 122 are connected to the dialysis machine 102, 200, 300, 400.

If the dialysis machine 102, 200, 300, 400 determines that the entire contents of the first and/or second bag 122a, 122b, is not fully delivered to the patient, then the system may alert or alarm at step 550 to alert the patient or user. In this manner, the amount of dialysate transferred to the patient as tracked by the dialysis machine 102, 200, 300, 400 may not match the expected volume of the dialysate bag 122, and/or the weight of the dialysate bag may not match the expected weight of the expected empty dialysate bag. The system may alarm or alert the patient or medical professional to check the system to make adjustments before continuing treatment. This series of verifications may be advantageous to ensure a full treatment regimen is delivered to a patient, as when less than 90% of a prescribed treatment is delivered to a patient, it may be considered ineffective. If a treatment volume delivered to the patient is less than a predetermined percentage of the total treatment volume, the dialysis machine 102, 200, 300, 405, 455 may alarm and may shut down without delivering any additional dialysate. For example, if the treatment volume delivered is less than 90% of the total treatment volume, the dialysis machine 102, 200, 300, 405, 455 may alarm or alert a user or medical professional that the treatment may be ineffective. In some embodiments, if a treatment volume delivered to the a predetermined percentage of the total treatment volume, but greater than a minimum percentage of the total treatment volume, the dialysis machine may complete treatment but also generate an alarm to notify the user or medical professional of the total treatment. For example, if the treatment volume delivered is greater than 90% of the total treatment volume, but less than 100%, the dialysis machine 102, 200, 300, 400 may complete the treatment but also alarm to notify the user or medical professional. Although the patient may receive an effective level of treatment, the alarm may alert the user to a condition of the dialysis machine 102, 200, 300, 400 to address before beginning another treatment.

The following may be examples of situations in which no air content is detected at step 515, negative pressure is detected at step 540, a line check is passed at step 545, and where the dialysate bag volume does not match the volume transferred to the patient at step 555. In one instance, this may occur if an incorrect dialysate bag is connected to the dialysis machine 102, 200, 300, 400, e.g., a 3 L bag is connected when the dialysis machine 102, 200, 300, 400 understands a 5 L or 6 L bag to be connected for a full treatment regimen (a smaller bag is connected when a larger bag is expected). Additionally, as described above, in some instances flexible containers of the dialysate bags, e.g., Biofine™, and/or PVC, may allow portions to close over the valves, creating a condition similar to a duckbill valve. Although fluid may be successively flowed in reverse to pass the line check, fluid flow may be restricted to prevent delivery of dialysate to the patient. Thus, the first and/or second bag 122a, 122b may still have a volume of dialysate for transfer (such that the comparison of bag volume transferred does not equal the bag volume of the attached bag at step 555). In these instances, an alert or alarm may be generated by the dialysis machine 102, 200, 300, 400, for a user or medical professional to check the system 100 and make adjustments before continuing treatment.

If the comparison of the bag volume transferred does approximately equal the volume of the first and/or second bag 122a, 122b at step 555, then the entire contents of the first and/or second bag 122a, 122b have been delivered to the patient, and the bag is empty. The process may then return to step 525 for determining if additional bags still have dialysate to transfer, and may follow the subsequent steps as described above.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method for operating a dialysis machine to conduct a dialysis treatment on a patient, comprising:
   transferring by a tubing dialysate from a first bag connectable to a dialysis machine;
   automatically determining the dialysate from the first bag has completely transferred;
   switching from the first bag to a second bag;
   transferring by the tubing dialysate from the second bag in response to the determination of the completed transfer of the first bag; and
   automatically determining the dialysate from the second bag has completely transferred;
   wherein the dialysis machine determines if an air content is detected in the transferred dialysate, such that:
      in response to detecting air content in the transferred dialysate, determining if the dialysate from the respective first or second bag has completely transferred; and
      in response to detecting no air content in the transferred dialysate, determining if negative pressure is detected in the tubing to the respective first or second bag.

2. The method according to claim 1, wherein the dialysate is transferred directly to the patient via a warmer pouch for in-line heating.

3. The method according to claim 1, wherein the dialysate is transferred to the patient via a heater bag for batch heating.

4. The method according to claim 3, wherein the dialysate is transferred to the heater bag during a dwell time of the dialysis machine.

5. The method according to claim 4, wherein the dialysate is transferred to the heater bag to a maintain a maximum capacity in the heater bag, thereby minimizing potential alerts or alarms.

6. The method according to claim 1, wherein the dialysis machine automatically determines a volume of the first bag or the second bag, or both, by one or more sensors for detecting a temperature, pressure, air content, flow, or weight, or combinations thereof, of the first bag or the second bag, or both.

7. The method according to claim 6, wherein the one or more sensors of the dialysis machine automatically detect a temperature, a pressure, air content, flow, or weight, or combinations thereof, of the dialysate for determining that transfer of the dialysate is complete.

8. The method according to claim 1, wherein the dialysis machine monitors a total treatment volume of dialysate transferred across all dialysate bags to determine completion of the dialysis treatment.

9. The method according to claim 1, wherein the first bag, the second bag, or both, are maintained in a vertical position or an inclined position when connected to the dialysis machine, such that an air content is disposed at a top portion of the first bag, or the second bag, or both.

10. The method according to claim 1, wherein when air content is detected in the transferred dialysate:
    in response to the dialysate completely transferring from the respective first or second bag, determining if additional dialysate bags are connected to the dialysis machine for transfer; and
    in response to the dialysate not completely transferring from the respective first or second bag, initiating an air management check prior to continuing dialysate transfer.

11. The method according to claim 1, wherein when no air content is detected in the transferred dialysate:
    in response to detecting a negative pressure in the tubing to the respective first or second bag, determining if the respective first or second bag passes a line check; and
    in response to not detecting a negative pressure in the tubing to the respective first or second bag, continuing to transfer dialysate from the respective first or second bag.

12. The method according to claim 11, wherein the line check includes flowing a volume of dialysate in reverse back to the respective first or second bag, wherein:
    in response to reaching the respective first bag or second bag, the dialysis machine determining if the respective first or second bag has completely transferred; and
    in response to failing to reach the respective first bag or second bag, the dialysis machine determining the tubing, the first bag, or the second bag, or combinations thereof, is kinked or blocked, or both.

13. The method according to claim 12, wherein the dialysis machine determines if the respective first or second bag has completely transferred by comparing a dialysate bag volume transferred to a detected volume of the respective first or second bag.

14. The method according to claim 12, wherein when the tubing, the first bag, or the second bag, or combinations thereof, is kinked, or blocked, or both, generating an alarm.

15. A dialysis system for conducting a dialysis treatment on a patient, comprising:
    a dialysis machine; and
    a first bag and a second bag connectable to the dialysis machine by a cartridge and tubing;
    wherein the dialysis machine is configured to:
       transfer by a tubing dialysate from the first bag;
       automatically determine the dialysate from the first bag has completely transferred;
       switch from the first bag to the second bag;
       transfer by the tubing dialysate from the second bag in response to the determination of the completed transfer of dialysate from the first bag; and
       automatically determine the dialysate from the second bag has completely transferred;
    wherein the dialysis machine is configured to determine if an air content is detected in the transferred dialysate, such that:

in response to detecting air content in the transferred dialysate, the dialysis machine being configured to determine if the dialysate from the respective first or second bag has completely transferred; and in response to detecting no air content in the transferred dialysate, the dialysis machine being configured to determine if negative pressure is detected in the tubing to the respective first or second bag.

16. The system according to claim 15, wherein the dialysate is transferable directly to the patient via a warmer pouch for in-line heating.

17. The system according to claim 15, wherein the dialysate is transferable to the patient via a heater bag for batch heating.

18. The system according to claim 17, wherein the dialysate is transferable to the heater bag during a dwell time of the dialysis machine.

19. The system according to claim 18, wherein the dialysate is transferable to the heater bag to maintain a maximum capacity in the heater bag, thereby minimizing potential alerts or alarms.

20. The system according to claim 15, wherein the dialysis machine automatically determines a volume of the first bag or the second bag, or both, by one or more sensors for detecting a temperature, pressure, air content, flow, or weight, or combinations thereof, of the first bag or the second bag, or both.

21. The system according to claim 20, wherein the one or more sensors of the dialysis machine automatically detects a temperature, a pressure, air content, flow, or weight, or combinations thereof, of the dialysate for determining that transfer of the dialysate is complete.

22. The system according to claim 15, wherein the dialysis machine monitors a total treatment volume of dialysate transferred across all dialysate bags to determine completion of the dialysis treatment.

23. The system according to claim 15, wherein the first bag, the second bag, or both, are connected to the dialysis machine in a vertical position or an inclined position such that an air content is disposed at a top portion of the first bag, the second bag, or both.

24. The system according to claim 15, wherein when air content is detected in the transferred dialysate by the dialysis machine:

in response to the dialysate completely transferring from the respective first or second bag, the dialysis machine being configured to determine if additional dialysate bags are connected to the dialysis machine for transfer; and in response to the dialysate not completely transferring from the respective first or second bag, the dialysis machine being configured to initiate an air management check prior to continuing dialysate transfer.

25. The system according to claim 15, wherein when no air content is detected in the transferred dialysate by the dialysis machine:

in response to detecting a negative pressure in the tubing to the respective first or second bag, the dialysis machine being configured to determine if the respective first or second bag passes a line check; and in response to not detecting a negative pressure in the tubing to the respective first or second bag, the dialysis machine being configured to continue transferring the dialysate from the respective first or second bag.

26. The system according to claim 25, wherein the line check includes the dialysis machine being configured to flow a volume of dialysate in reverse back to the respective first or second bag, wherein:

in response to reaching the respective first bag or second bag, the dialysis machine being configured to determine if the respective first or second bag has completely transferred; and in response to failing to reach the respective first bag or second bag, the dialysis machine being configured to determine that the tubing, the first bag, or the second bag, or combinations thereof, is kinked or blocked, or both.

27. The system according to claim 26, wherein the dialysis machine is configured to determine if the respective first or second bag has completely transferred by comparing a dialysate bag volume transferred to a detected volume of the respective first or second bag.

28. The system according to claim 26, wherein when the tubing, the first bag, or the second bag, or combinations thereof, is kinked, or blocked, or both, the dialysis machine being configured to generate an alarm.

* * * * *